United States Patent [19]
Baba et al.

[11] Patent Number: 6,037,489
[45] Date of Patent: Mar. 14, 2000

[54] METHOD OF PURIFYING GLYOXYLIC ESTERS AND DISTILLATION EQUIPMENT FOR PURIFYING GLYOXYLIC ESTERS

[75] Inventors: Hideyuki Baba, Osaka; Satoru Miura, Ibaraki; Masanori Nonoguchi, Minoo; Noboru Saito, Takatsuki, all of Japan

[73] Assignee: Nippon Shokubai Co., Ltd., Japan

[21] Appl. No.: 09/051,302

[22] PCT Filed: Aug. 9, 1997

[86] PCT No.: PCT/JP97/03043

§ 371 Date: Apr. 10, 1998

§ 102(e) Date: Apr. 10, 1998

[87] PCT Pub. No.: WO98/09936

PCT Pub. Date: Mar. 12, 1998

[30] Foreign Application Priority Data

Sep. 5, 1996 [JP] Japan .................................. 8-235529

[51] Int. Cl.[7] .............................. C07C 69/66; C07C 51/46
[52] U.S. Cl. .............................. 560/177; 560/186; 203/2; 203/14; 203/28
[58] Field of Search .................................. 560/186, 177; 203/2, 14, 28

[56] References Cited

U.S. PATENT DOCUMENTS

| | | | |
|---|---|---|---|
| 1,614,195 | 1/1927 | Haussler | 560/174 |
| 4,156,093 | 5/1979 | Christidis | 560/186 |
| 4,340,748 | 7/1982 | Baltes et al. | 560/177 |
| 4,502,923 | 3/1985 | Dyroff et al. | 203/71 |
| 4,814,491 | 3/1989 | Driscoll et al. | 560/186 |
| 4,867,849 | 9/1989 | Cova et al. | 203/28 |
| 5,217,582 | 6/1993 | Heinsohn et al. | 203/78 |

FOREIGN PATENT DOCUMENTS

| | | |
|---|---|---|
| 60-23345 | 2/1985 | Japan . |
| 1-254643 | 10/1989 | Japan . |
| 2-73040 | 3/1990 | Japan . |

OTHER PUBLICATIONS

Cova, D.R. et al, "Distillation of Reactive Methyl Glyoxylate–Methyl Glycolate Mixtures", Separation Science and Technology, 1990, vol. 25, No. 13–15, pp. 1981–1991.

Japanese Examined Patent Publication No. 4–66856/1992 (Tokukohei 4–66856 Published Oct. 26, 1992).

Lide, binary systems, CRC Handbook of Che.& Physics: 6–217, Mar. 1994.

Primary Examiner—Gary Geist
Assistant Examiner—Taylor V. Oh
Attorney, Agent, or Firm—Nixon & Vanderhye

[57] ABSTRACT

A method for purifying glyoxylates includes (1) a coarse distillation process in which a crude glyoxylate in which water coexists is, in a film form, continuously subjected to coarse distillation, and (2) an azeotropic dehydration process in which the crude glyoxylate purified through the coarse distillation process is subjected to azeotropic dehydration in the presence of an azeotropic agent such as propyl acetate. By this method, high-purity glyoxylates can be efficiently and easily obtained at lower costs.

11 Claims, 4 Drawing Sheets

METHOD OF PURIFYING GLYOXYLIC ESTERS AND DISTILLATION EQUIPMENT FOR PURIFYING GLYOXYLIC ESTERS

TECHNICAL FIELD

The present invention relates to a method for purifying glyoxylates and a distiller for purification of glyoxylates.

BACKGROUND ART

Glyoxylates are chemical intermediates, for example, monomers suitably used as material for synthesizing sodium polyglyoxylate which is an effective builder component of a surface active agent.

In the case where the glyoxylates to be used as material for forming polymers contain impurities, particularly protic compounds such as water, alcohols, or carboxylic acids, a molecular weight of the resultant polymer tends to decrease. Therefore, when such glyoxylates are used as material for copolymers, the impurities have to be removed from the glyoxylates.

However, since the glyoxylates reversibly combine with water or alcohols in particular thereby forming hydrate, hemiacetal, or the like, to purify the glyoxylates is not easy.

The following purifying methods applicable to the glyoxylates have been proposed:

(1) executing distillation, with phosphoric anhydride added to a material containing glyoxylates;

(2) adding a higher alcohol with a boiling point of not lower than 180° to a material containing glyoxylates, and executing distillation at a pressure not exceeding 800 mmHg (107 kPa) (the Japanese Publication for Laid-Open Patent Application No.62-178541/1987 (Tokukaisho 62-178541));

(3) distilling a mixture containing glyoxylates, glycolates, water, alcohols, and the like under a reduced pressure so that a content of water and alcohols decreases to less than 1 weight percent (wt. %), then, distilling it by adjusting so that a molar ratio of glycolate to glyoxylates becomes 1 to 1.4 (the Japanese Examined Patent Publication No.5-28694/1993 (Tokukohei 5-28694), the Japanese Publication for Laid-Open Patent Application No.60-97936/1985 (Tokukaisho 60-97936));

(4) when glyoxylates are produced from corresponding glycolates by oxidative dehydrogenation in a gaseous phase, adding an azeotropic agent such as methylene chloride, chloroform, n-pentane, cyclohexane, nonane, di-isopropyle ether, methyl ethyl ketone, benzene, toluene, or the like to a gaseous reaction mixture resulting on the oxidative dehydrogenation, and introducing the same to a distillation column (the Japanese Publication for Laid-Open Patent Application No.60-23345/1985 (Tokukaisho 60-23345));

(5) esterifying glyoxylic acid by reacting 1 mol of glyoxylic acid with 0.5 to 2 mol of lower alcohol in the presence of an azeotropic agent such as benzene or dichloroethane, and distilling the same after a concentration of water and alcohol in the reactive solution becomes not more than 10 wt. % each with respect to the resultant glyoxylates (the Japanese Publication for Laid-Open Patent Application No.61-50941/1985 (Tokukaisho 61-50941), the Japanese Examined Patent Publication No.4-66856/1992 (Tokukohei 4-66856)); and (6) processing a reaction product obtained by oxidative dehydrogenation with respect to glycolates under a reduced pressure, then, supplying the reaction product thus processed to a multi-stage distillation column which holds a dense azeotropic agent such as methylene-dichloride, 1,1,1-trichloroethane, or benzene in the vicinity of its top, so that glyoxylates are taken from an intermediate point between the supplying part and the top part of the distillation column (the Japanese Examined Patent Publication No.7-42252/1995 (Tokukohei 7-42252), the Japanese Publication for Laid-Open Patent Application No.2-73040/1990 (Tokukaihei 2-73040), the Japanese Examined Patent Publication No.7-45435/1995 (Tokukohei 7-45435), the Japanese Publication for Laid-Open Patent Application No.1-254643/1989 (Tokukaihei 1-254643), the Japanese Examined Patent Publication No.5-28694/1993 (Tokukohei 5-28694)).

However, the method (1) is not preferable from an economic viewpoint, since phosphoric anhydride is consumed reacting with water or alcohols and hence it is hardly recovered. The method (2) has a drawback in that side reactions such as ester interexchange and the like may possibly occur. Moreover, since the method (3) requires excessive glycolates, the method (3) has a drawback in that productivity lowers due to the presence of the excessive glycolates. For these reasons, it is impossible to efficiently produce high-purity glyoxylates by the above methods (1) through (3).

Furthermore, as a result of various examinations by the inventors of the present application, the azeotropic agents used in the methods (4) and (5) exhibit insufficient performances, and high-purity glyoxylates are hardly obtained at a high yield with the use of the above azeotropic agents. Besides, in the case where a chemical compound such as benzene or trichloroethane is used as an azeotropic agent as in the case of the method (6), such a compound is toxic and it is difficult to deal with it.

In the aforementioned conventional methods, prior to a purification process whereby water is removed by azeotropy, coarse distillation for preliminarily concentrating glyoxylates in crude glyoxylates is carried out so that the purification is efficiently conducted, by utilizing a distillation column.

However, by the above conventional methods, the glyoxylates in the crude glyoxylates are, during coarse distillation, subjected to heating for a long period of time thereby becoming hydrolyzed. This causes a yield of the glyoxylates obtained through the purification process to decrease, thereby disenabling efficient production of high-purity glyoxylates.

Moreover, by the conventional methods, the glyoxylic acid produced through hydrolyzation is further resolved by a subsequent distillation process, thereby producing side products. Therefore, a content of the glyoxylates to be obtained lowers, leading to a drawback in that a purification efficiency of the glyoxylates deteriorates.

DISCLOSURE OF THE INVENTION

The object of the invention is to provide a method for purifying glyoxylates and a distiller for purifying glyoxylates, whereby the high-purity glyoxylates can be efficiently and conveniently obtained at lower costs.

As a result of the inventors' eager study in order to achieve the above object, it was found that by continuously conducting coarse distillation with respect to a crude glyoxylate in a film form in which water coexists, and/or distilling the same with the use of aliphatic ester as azeotropic agent, high-purity glyoxylate can be efficiently and conveniently obtained at lower costs. The present invention was completed based on this finding.

It should be noted that it has not yet been known that in the purification of the glyoxylates, an excellent dehydrating effect can be achieved by using aliphatic esters as azeotropic agents, and as a result high-purity glyoxylates can be obtained.

Specifically, to achieve the above object, the method of the present invention for purifying the glyoxylates is characterized in comprising an azeotropic dehydration step of conducting azeotropic dehydration with respect to a crude glyoxylate in which water coexists, in the presence of an aliphatic ester as an azeotropic agent.

By the foregoing method, removal of water from the crude glyoxylate can be efficiently carried out by using the aliphatic ester as the azeotropic agent. This ensures that a high-purity glyoxylate suitable as a polymer material can be efficiently and easily obtained at lower costs. Moreover, the purifying method of the present invention is superior in safety and handling, since, unlike the conventional methods, a toxic chemical compound is not used as an azeotropic agent.

Furthermore, to achieve the aforementioned object, another method of the present invention for purifying the glyoxylates is characterized in comprising a coarse distillation step of continuously conducting coarse distillation with respect to a crude glyoxylate in a film form in which at least water coexists, and a main distillation step of further distilling a crude purified liquid obtained by the coarse distillation step, the liquid containing glyoxylate.

According to the foregoing method, low-boiling-point components such as water which have lower boiling points than that of the glyoxylate are decreased in the crude glyoxylate by coarse distillation process, and subsequently, the coarsely purified liquid is purified by the main distillation process. As a result, a high-purity glyoxylate is obtained.

Besides, in the above method, by continuously conducting the coarse distillation with respect to the glyoxylate in a film form, a heating time in the coarse distillation with respect to the crude glyoxylate is decreased as compared with cases where conventional distillation columns are used. Therefore, hydrolization of the glyoxylate in the coarse distillation is suppressed, allowing a high-purity glyoxylate to be obtained at a high yield.

Furthermore, by making the main distillation process include the aforementioned azeotropic dehydration process using the azeotropic agent, it is possible to obtain high-purity glyoxylates at further higher yield.

For a fuller understanding of the nature and advantages of the invention, reference should be made to the ensuing detailed description taken in conjunction with the accompanying drawings.

BEST MODE FOR CARRYING OUT THE INVENTION

The following description will explain an embodiment of the present invention in detail.

A method of the present invention for purifying glyoxylates is a method wherein coarse distillation is continuously conducted with respect to a crude glyoxylate in a film form, in which water coexists, and/or the crude glyoxylate is distilled with the use of an aliphatic ester as an azeotropic agent. Example of such a glyoxylate to be processed are compounds which are expressed by the following formula (1):

where $R_3$ represents an organic residual group.

In the formula (1), a substituent represented by $R_3$ is not particularly limited as long as it is an organic residual group. Examples of the substituent include hydrocarbon groups such as a methyl group, an ethyl group, an n-propyl group, an isopropyl group, an n-butyl group, a sec-butyl group, and a tert-butyl group.

In other words, no specific glyoxylates are preferred, but concretely speaking, examples of the glyoxylates include methyl glyoxylate, ethyl glyoxylate, n-propyl glyoxylate, isopropyl glyoxylate, n-butyl glyoxylate, sec-butyl glyoxylate, and tert-butyl glyoxylate. The purifying method of the present invention is effectively applied to methyl glyoxylate in particular among the glyoxylates.

The glyoxylates processed by the method of the present invention are compounds which are preferably used as chemical intermediates, such as monomers for synthesizing sodium polyglyoxylate which is an effective builder component such as a surface active agent. No specific method for producing the glyoxylates is particularly preferable, and various methods which have conventionally been known can be used. For example, oxidization in a gas phase is conducted with respect to (1) glyoxal and/or glycol aldehyde, plus (2) alcohol or olefin, in the presence of oxygen and a catalyst. By doing so, desired crude glyoxylates can be easily obtained. Besides, production conditions of the glyoxylates, that is, reaction conditions such as a reaction temperature and a reaction time are not particularly limited. They may be appropriately set so that the reaction is completed.

The glyoxylates resulting on the reaction, that is, the crude glyoxylates not yet purified, contain, as side products of the reaction, a plurality of impurities such as components having lower boiling points than those of the glyoxylates. The crude glyoxylates may be used as they are, but in the case where they are used as polymer materials, contents of the impurities, particularly protic compounds such as water, alcohols, and carboxylic acids have to be sufficiently small.

However, the glyoxylates reversibly react with water or alcohols in particular among the impurities, thereby forming hydrates, hemiacetal, or the like, and hence to purify the glyoxylates is not easy.

Figure 1:
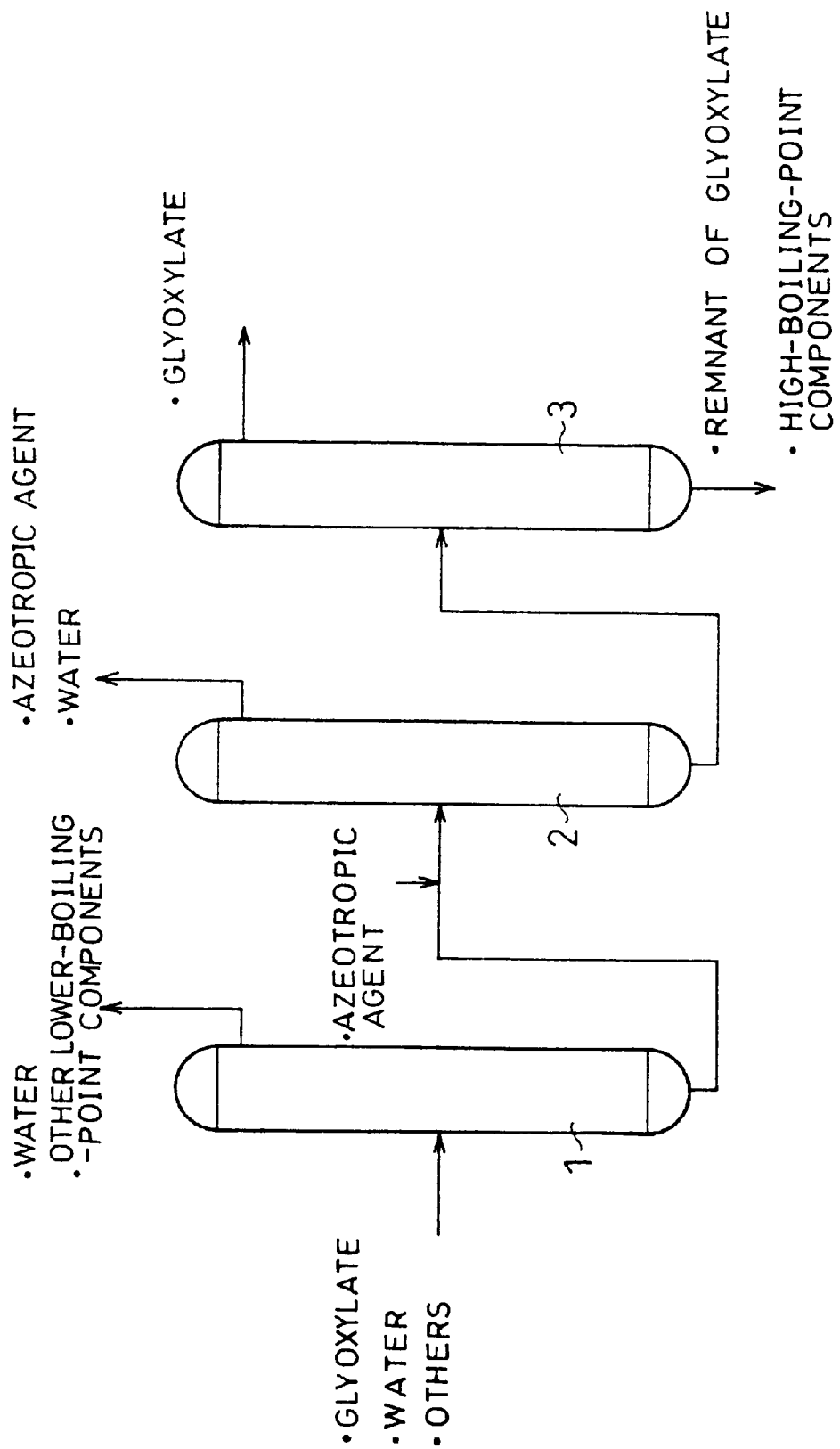
FIG. 1 is a schematic view illustrating an arrangement of each distiller of the present invention which is used for purifying glyoxylates.

The following description will explain, referring to FIG. 1, an example of a concrete purifying method of the present invention applied to the glyoxylates, that is, a sequence of distillation processes including the azeotropic dehydration.

The sequence of distillation processes of the present invention including the azeotropic dehydration can be carried out by performing the following two steps in this order: (i) a coarse distillation step for obtaining crude purified liquid by removing a majority of low-boiling-point components from a treated liquid which is a crude glyoxylate containing the low-boiling-point components; and (ii) a main distillation step for further purifying the crude purified liquid by distillation. In the coarse distillation step, from a liquid of the crude glyoxylates containing low-boiling-point components such as water, a majority of the low-boiling-point components are removed, so that the crude purified liquid is obtained.

The main distillation step includes an azeotropic dehydration step whereby an azeotropically purified liquid is obtained by removing residual water from the crude purified liquid by azeotropic dehydration, and a fractionating step whereby the glyoxylates of high purity (not less than 95 percent) are obtained from the azeotropically purified liquid by fractionating.

In each step, any scheme of a batch distillation type or a continuous distillation type can be applicable by the use of various conventional distillation devices. The following description will explain the sequence of processes composed of the coarse distillation step, the azeotropic dehydration step, and the fractionating step, taking as an example a case where the continuous distillation scheme is applied to each step.

It is preferable to start the process sequence with continuous coarse distillation with respect to a crude glyoxylate in a film form. The crude glyoxylate is a material mixture containing a glyoxylate, and low-boiling-point components including water. In the above step, to perform the coarse distillation as described above, it is preferable to remove from the crude glyoxylate a majority of low-boiling-point components including water which are contained in the crude glyoxylate, by utilizing a thin film evaporator (a liquid-film-type distillation device, a low-boiling-point component distillation device) 1.

It should be noted that operational conditions such as a temperature, a pressure, and a rate of supply of the material may be appropriately set, in accordance with a composition of the material mixture, but it is desirable that the operation is carried out at as low a pressure as possible so that a temperature of a bottom product becomes low, with view to lowering the heat history. On the other hand, if the operation is carried out at an extremely low pressure, an excessive performance is required of a condenser for recovering distillate vapor, thereby leading to economic disadvantages. A preferable pressure range is 30 mmHg to 760 mmHg (4kPa to 101 kPa), and a more preferable range is 200 mmHg to 500 mmHg (27 kPa to 67 kPa).

Furthermore, from a viewpoint of suppressing the heat history during the operation, a residence time of the crude glyoxylate in the coarse distillation step is preferably as short as possible in a range such that as uniform a film as possible is formed. On the other hand, from a viewpoint of improving the purification efficiency in the coarse distillation step, the residence time is preferably long. Therefore, in practice, the residence time is preferably set in a range of 0.1 to 20 minutes, and more preferably in a range of 0.1 to 10 minutes.

The liquid film in the coarse distillation step preferably has a small thickness in a range such that the film is uniformly formed. Concretely, a preferable range of the thickness is 0.1 to 3 mm, and a more preferable range is 0.1 to 2 mm. Furthermore, a range of 0.1 to 1 mm is particularly preferable.

The bottom product, that is, for example, the bottom product from the column bottom of the thin-film evaporator 1 is used as a material subjected to the subsequent azeotropic dehydration step. A predetermined quantity of an azeotropic agent, for example, 0.5 to 4 times a volume of the bottom product, is added to the bottom product resulting on the foregoing coarse distillation operation (step), and it is used as the material in the azeotropic dehydration step.

The material is continuously supplied to a material supply stage which is provided between the column top and the column bottom of an azeotropic dehydration column (distillation column) 2, through a material supply tube (not shown). Note that a position of the material supply tube in the azeotropic dehydration column 2, that is, a position of the material supply stage, is not particularly limited. Besides, the processed liquid through the azeotropic dehydration is continuously taken out of the processing system, that is, the azeotropic dehydration column 2, as a bottom product and a distillate, through a bottom product discharging tube and a distillate discharging tube which are not shown.

Here, the bottom product discharging tube may be set, for example, at the bottom (the lowest stage) of the azeotropic dehydration column 2, while the distillate discharging tube may be set at the top (the highest stage) of the azeotropic dehydration column 2, but there is no particular limitation on their positions. By doing so, a distillate composed of an aliphatic ester as the azeotropic agent, water, and other low-boiling-point components is obtained from the distillate discharging tube (column top) of the azeotropic dehydration column 2, while a bottom product composed of (i) a glyoxylate, (ii) hemiacetal resulting on reaction between a glyoxylate and alcohols including glycolates, ethylene glycol, and the like, and (iii) other higher-boiling-point impurities is obtained from the bottom product discharging tube (column bottom).

Processing conditions in the azeotropic dehydration step, i.e., the number of stages of the azeotropic dehydration column 2, a temperature, a pressure, and an material supply amount (supply rate), and others are not particularly limited, but are appropriately determined by experiments or computations depending on a composition of the material. However, the operation is preferably executed so that water and the azeotropic agent remaining in the bottom product account for not more than 0.2 wt. % and not more than 0.5 wt. %, respectively. Besides, such azeotropic dehydration process may be repeated a plurality of times if necessary, to achieve a higher dehydrating effect. For example, in the case where the azeotropic dehydration process is conducted twice, the first operation may be carried out in conditions such that the azeotropic agent is distributed to the column bottom so that the crude glyoxylate and the azeotropic agent are brought into full contact with each other in the column, and the second operation may be carried out in operational conditions such that the azeotropic agent does not reach the column bottom so that the azeotropic agent would not remain in the bottom product.

The bottom product is used as a material subjected to the subsequent fractionating process. From an economic viewpoint, however, it is preferable that the aliphatic esters in the distillate are separated from water by gravity separation and are purified and re-used.

Subsequently, in the fractionating process, the bottom product obtained through the previous azeotropic dehydration operation (process) is continuously supplied to a supply stage provided between a column top and a column bottom of a fractionating distillation column (distillation column) 3, so as to be used as a material subjected to the fractionating process. By doing so, a high-purity glyoxylate is obtained as distillate from, for example, the column top of the fractionating distillation column 3, while a bottom product composed of a residual glyoxylate, hemiacetals of the glyoxylate and alcohols, and other high-boiling-point impurities is obtained from, for example, the column bottom of the fractionating distillation column 3.

Furthermore, from an economic viewpoint, it is preferable that the bottom product of the fractionating distillation column 3 is supplied to another distillation column so that high-boiling-point residues are separated therefrom, and the glyoxylate and hemiacetals of the glyoxylates which are left may be returned to the azeotropic dehydration process.

An aliphatic ester is preferable as an azeotropic agent applied to the azeotropic dehydration process. The glyoxylates are purified easily and safely by azeotropic dehydration with the use of such aliphatic ester.

The exact reason why the aliphatic esters are effective as the azeotropic agents is still unknown, but it is presumed that it may be related to properties of the aliphatic esters, namely, sufficient affinity with the glyoxylates and a small compatibility with water.

The aliphatic esters used as the azeotropic agents in the present invention are not particularly limited, but to be more concrete, compounds expressed by the following formula (2) are given as examples of the same:

$$R_1COOR_2 \qquad (2)$$

where $R_1$ represents hydrogen, a methyl group, or an ethyl group, while $R_2$ represents an alkyl group with 1 to 4 carbons. Among these aliphatic esters, n-propyl acetate and isopropyl acetate are particularly preferable.

Any one of the aliphatic esters forms a low-boiling azeotropic mixture with water. The low-boiling azeotropic mixtures have azeotropic points, respectively, which are sufficiently lower than those of the glyoxylates. Moreover, the compatibility thereof with water is low, and hence they are easily separated from water by gravity separation. Therefore, if particularly necessary, it is possible to purify them for re-use.

A quantity of an aliphatic ester to be added to a crude glyoxylate is not particularly limited, and processing conditions such as a temperature, a pressure, and a processing time (the number of distillation column stages) of the process system are not particularly limited, either. However, the temperature in the system is preferably high within a range such that a side reaction does not occur, so that separation and removal of water which exists chemically combined with the glyoxylate is promoted.

A method for adding the aliphatic esters is not particularly limited, and various conventional methods are applicable. Among them, the following method is preferable: a desired set amount of an aliphatic ester is added to, and mixed with, a crude glyoxylate in advance, and the resultant mixture is continuously supplied to, for example, a middle stage of the distillation column. More preferable is the following method: the glyoxylates are supplied to the distillation column in advance, and after a majority of low-boiling-point components such as water is removed from the same by the coarse distillation operation, a desired set amount of the aliphatic ester is added to and mixed with the remnant (residue), and thereafter, the mixture is continuously supplied to, for example, a middle stage of the distillation column.

According to the present invention, by the use of the aliphatic esters as the azeotropic agents, water is easily removed from the crude glyoxylates due to the azeotropic dehydration. By doing so, high-purity glyoxylates which are preferably used as polymer materials are efficiently and easily obtained at lower costs.

Moreover, the purifying method of the present invention is superior in safety and handling, since, unlike the conventional methods, a toxic chemical compound is not used as an azeotropic agent. On top of that, the glyoxylates purified by the aforementioned purifying method have high quality, and are suitably applied to the aforementioned purposes.

As a thin-film evaporator (liquid-film-type distillation device) 1 applied to the coarse distillation process, various public known liquid-film-type evaporators are applicable. The liquid-film-type evaporators are evaporators wherein treated liquid is formed in a thin film form and is brought into contact with a heated surface. Such evaporators are classified into the categories such as an ascending film type, a falling film type, and a forced agitation type. Among them, either the falling film type or the forced agitation type is preferable for the present invention.

Figure 2:
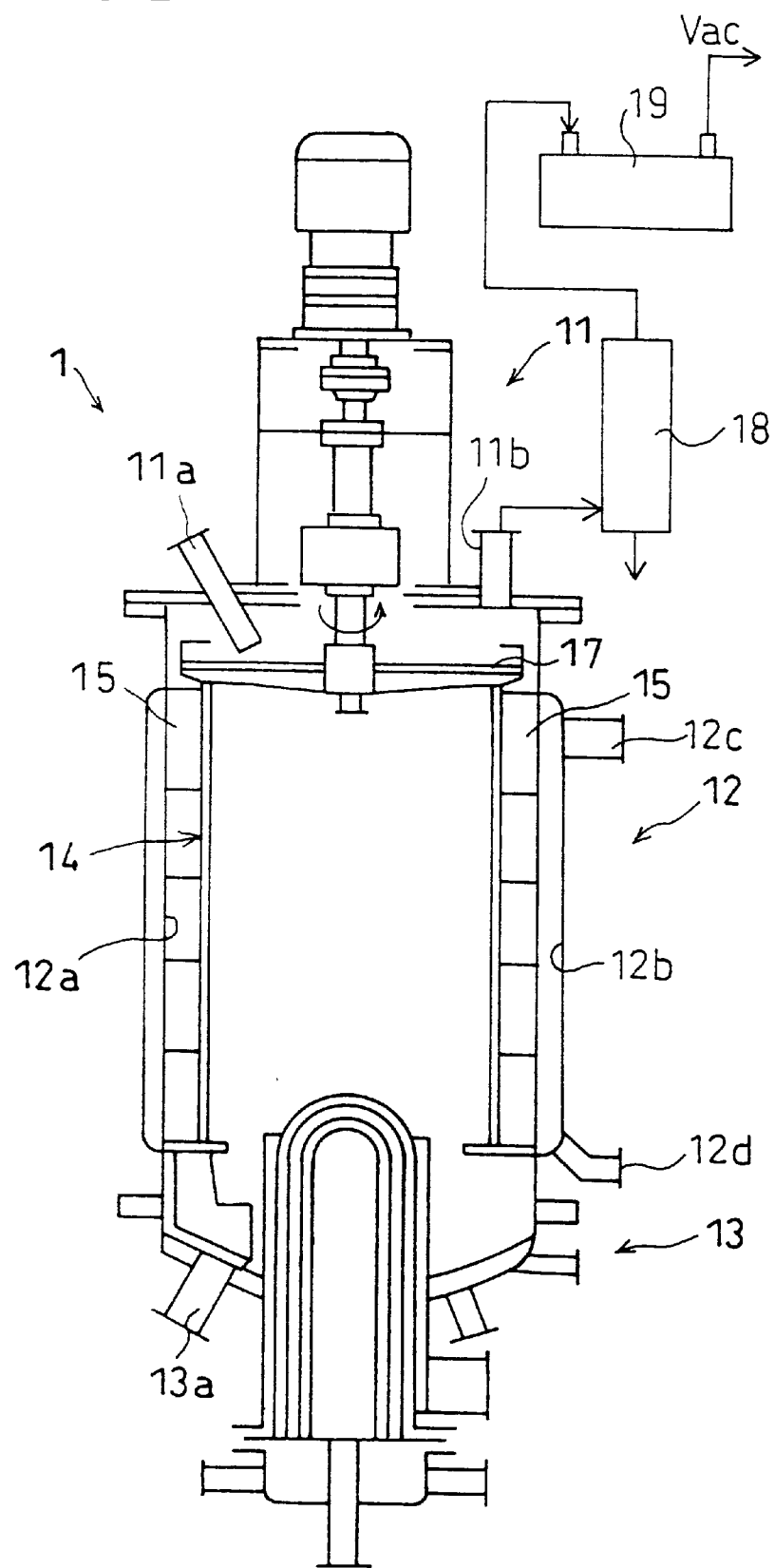
FIG. 2 is a schematic vertical cross-sectional view of a forced-agitation-type thin film evaporator used in the coarse distillation process in each distiller.
Figure 3:
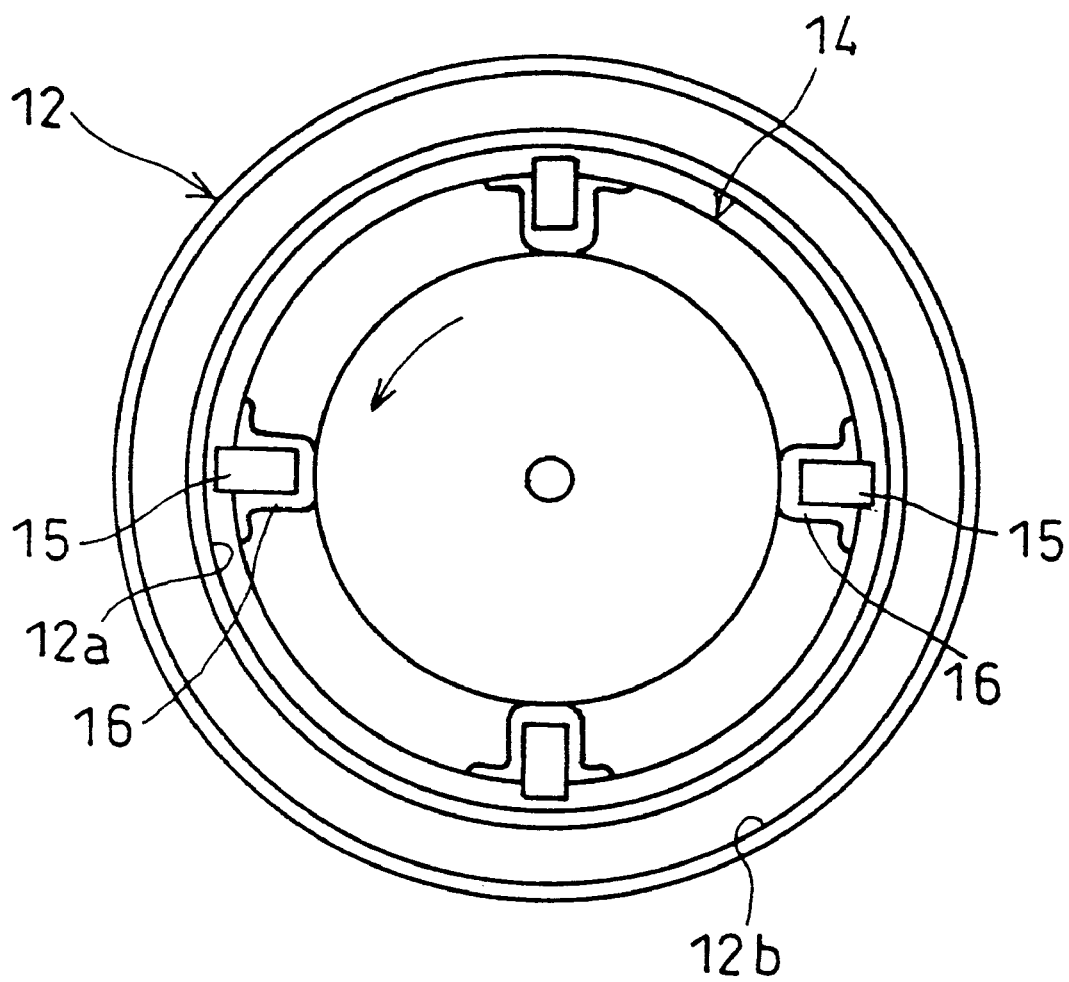
FIG. 3 is a schematic horizontal cross-sectional view of the thin film evaporator.
Figure 4:
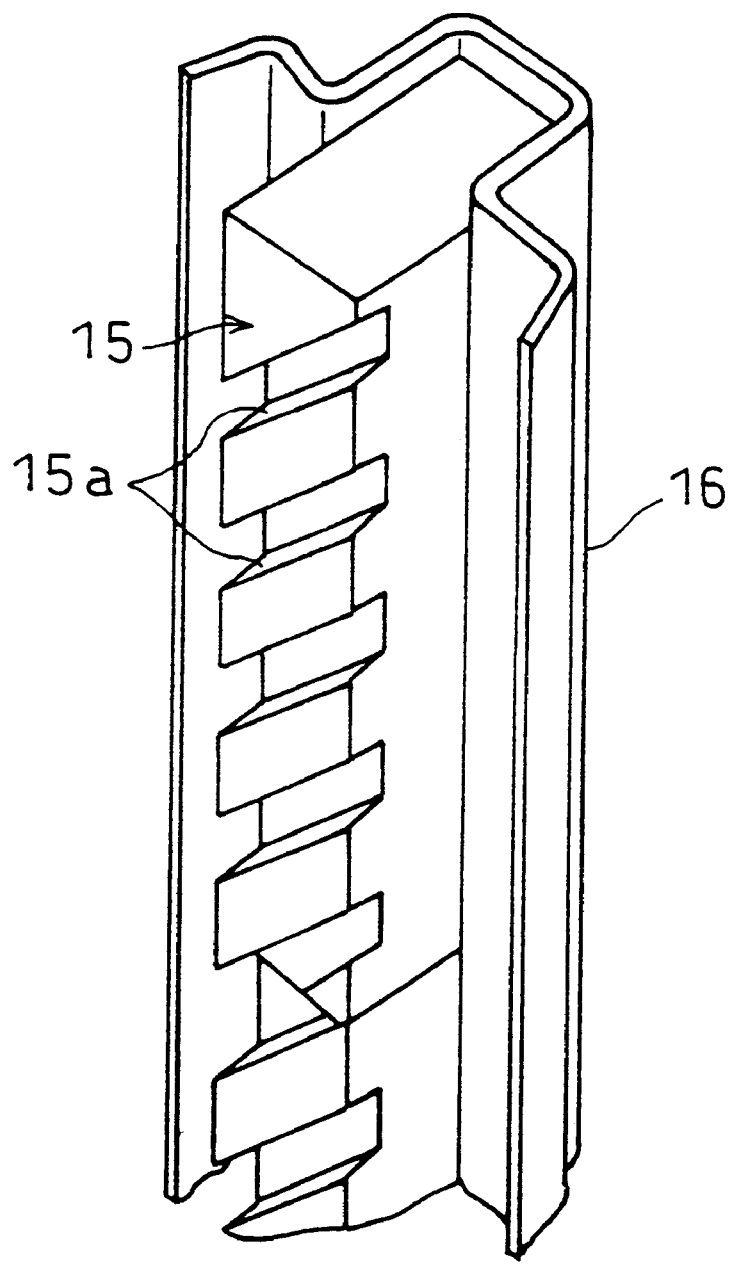
FIG. 4 is a perspective view of a wiper and a wiper supporter of the thin film evaporator.

As the thin film evaporator 1 of the forced-agitation liquid-film type, one shown in FIGS. 2 through 4 is taken as example, which is equipped with a rotary vane for agitating the treated liquid while controlling a thickness of the liquid film.

The thin film evaporator 1 is equipped with, from the top, a driving unit 11 for driving a motor and the like, an evaporating-condensing unit 12 in a cylindrical form beneath the driving unit 11, and a liquid receiving unit 13 in a cylindrical form with a bottom, which is connected with the evaporating-condensing unit 12.

Inside the evaporating-condensing unit 12, a rotor 14 driven by the driving unit 11 is rotatably provided so as to be coaxial with the evaporating-condensing unit 12. Therefore, a circumferential surface of the rotor 14 is at a substantially uniform distance from an evaporating surface as an inner surface of the evaporating-condensing unit 12, that is, a heating surface 12a. The evaporating-condensing unit 12 is equipped with a jacket 12b for controlling a temperature of the heating surface 12a by passage of heated water or the like so that the jacket 12b covers an outer surface of the wall having the heating surface 12a inside.

On the circumferential surface of the rotor 14, there are installed wipers 15 for rubbing an inner surface of the evaporating-condensing unit 12. The wipers 15 are formed in a rectangular blade shape each, so that their lengthwise direction conforms an axial direction of the rotor 14, and they can be extruded in radial directions of the rotor 14. Therefore, on the circumferential surface of the rotor 14, there are provided wiper holding members 16, which are formed in a groove form each for holding the wipers 15 so that the wipers 15 are freely extruded therefrom and accommodated therein. A plurality of the wiper holding members 16 are provided thereon at regular intervals in a circumferential direction of the rotor 14.

Furthermore, on a rubbing surface of each wiper 15, a plurality of grooves 15a are provided (1) so as to be oblique with respect to a rubbing direction, with their head ends being on an upstream side of the falling treated liquid, while their rear ends being on a downstream side of the treated liquid, and (2) so as to be parallel with each other.

On a top of the rotor 14, there is provided a liquid distributing disk 17 in a disk form which rotates in an interlocked manner with the rotor 14. The liquid distributing disk 17 has a plurality notched nozzles (not shown) on its circumferential surface. The notched nozzles are to evenly distribute the treated liquid over the inner surface of the heating surface 12a by using the centrifugal force, the treated liquid being to become the crude glyoxylates through the process and being supplied into the evaporating-condensing unit 12 through a material inlet 11a.

The aforementioned driving unit 11 is adjusted depending on the size and other factors of the evaporating-condensing unit 12 so that the rotor 14 has an appropriate number of rotations corresponding to a circumferential speed of about 4 to 5 m/s. Besides, shaft seal parts (not shown) of the driving unit 11 are provided with mechanical seals, whereby sealing is enabled in high vacuum at a level of $10^{-4}$ Torr (0.013 Pa).

The liquid receiving unit 13 is equipped with a condensed liquid discharging outlet 13a through which the remnant is taken out as a bottom product (crude purified liquid). There may be provided a scraper (not shown) in a bottom part of the rotor 14, so that the scraper pushes out the remnant that now has a high viscosity, through a lower part of the heating surface 12a to the liquid receiving unit 13.

Furthermore, mist separators (not shown) for separating mist of the treated liquid from vapor and returning it to the treated liquid may be provided between neighboring wipers 15.

In addition, a recovering column 18 with a necessary minimum number of distillation stages for recovering the glyoxylate contained in vapor discharged from the column top may be provided to a vapor outlet 1b of the thin film evaporator 1. The number of the distillation stages and a height of packing section are appropriately determined depending on a distillate composition, operational conditions, a type of a column packing, and the like. A condenser 19 for recovering toxic components contained in the vapor discharged from the column top of the recovering column 18, such as an organic solvent, may be connected with the recovering column 18. The thin film evaporator 1 is vacuumed through the condenser 19, and by doing so, the pressure-reduced state in the thin film evaporator 1 is maintained.

The following description will explain operations of the thin film evaporator. First, the treated liquid supplied through the material inlet 11a is distributed through each notched nozzle of the liquid distributing disk 17 by the centrifugal force evenly over the heating surface 12a. The heating surface 12a to which the treated liquid is thus evenly applied is rubbed by the wipers 15, which are pressed against the heating surface 12a by the centrifugal force due to the rotation of the rotor 14. Therefore, each wiper 15 contributes to form a thin film of the treated liquid with a uniform thickness (0.1 to 3 mm) on the heating surface 12a, while renewing a surface portion of the treated liquid film.

Each groove 15a of the wipers 15 prevents scatter of the treated liquid which may be caused by the wipers 15, and, since each groove 15a is formed obliquely with respect to the rubbing direction, it deliberately causes the treated liquid to go down in the liquid falling direction.

Here, vapor of the treated liquid (crude glyoxylate) flowing down on the heating surface 12a is taken out from the thin film evaporator 1 through the vapor outlet 11b provided on the column top thereof, by sucking. On the other hand, a heat medium (heated water or pressurized steam) is sent in through a heat medium inlet 12d in a lower portion of the jacket 12b, while the heat medium is taken out through a heat medium outlet 12c in an upper portion of the jacket 12b.

By supplying the heat medium in such a direction, the jacket 12b for controlling the temperature of the heating surface 12a is caused to have such a temperature gradient as causes a temperature of the heating surface 12a gradually to lower in a direction reverse to a moving direction of the treated liquid on the heating surface 12a. This vapor sucking direction and this heat medium supplying direction makes the coarse distillation of the treated liquid (crude glyoxylate) efficient.

Thus, by the above method, low-boiling-point components including water is continuously removed from the treated liquid by distillation, by keeping the treated liquid in a film form with a uniform thickness while allowing it to flow down, preferably at a reduced pressure realized by discharging vapor through the vapor outlet 11b.

Thus, by the above method wherein the treated liquid, in a film form, is continuously processed, the heat conduction efficiency with respect to the treated liquid is enhanced, thereby enabling quick removal of the low-boiling-point components in the treated liquid. Therefore, a time while the treated liquid stays on the heating surface 12a, that is, a heating time, can be reduced, as compared with a case where a conventional distillation column is used.

Thus, the above method has the following advantages: (1) hydrolization of the glyoxylate in the treated liquid which tends to occur in the distilling process when the heating time increases is avoided, thereby efficiently increasing the content of the glyoxylates in the crude glyoxylates obtained through the coarse distillation process; and (2) production of glyoxylic acids which are impurities generated in the hydrolization is avoided.

Therefore, by the aforementioned method, the efficient purification of the glyoxylate is enabled with simple operations. Besides, by the aforementioned method, a composition of the vapor discharged is kept substantially uniform by continuously processing the treated liquid in a film form. Therefore, in the case where the recovering column is provided at the vapor outlet, even if recovering conditions are kept constant, degradation of the recovery efficiency is avoidable in the aforementioned method. As a result, the purification of the glyoxylates is simplified while the high yield is ensured.

It should be noted that a case where the thin film evaporator of the falling film type is used in the coarse distillation process is taken as example to explain the above method, but it is possible to use a thin film evaporator of the liquid film ascending type.

In such a liquid-film-ascending-type evaporator, by boiling the treated liquid in a vertical long tube, the remnant of the treated liquid ascends accompanying the rise of generated vapor. As the remnant rises upwards, it comes to boil, and a quantity of the vapor gradually increases in an upper part of the long tube. Therefore, bubbles in the long tube grow, and in a further upper part of the tube, vapor rapidly rises therethrough, causing the remnant to rise in a film form along the tube wall. Thus, from the remnant which ascends in the film form, the low-boiling-point components are efficiently removed.

Furthermore, in the above description on the aforementioned method, (1) a case where the thin film evaporator 1 is used in the coarse distillation process, and (2) a case where one of the aliphatic esters is used as an azeotropic agent in the azeotropic dehydration process, are separately explained, but combination of these may be applicable. By such combination, the efficiency in purification of the glyoxylates is heightened.

The following description will more concretely explain the present invention, by showing examples and comparative examples, but the present invention is not limited by these examples.

[EXAMPLE 1]

(1) Coarse distillation Process

To start with, methanol accounting for 53.0 wt. %, water accounting for 22.0 wt. %, formaldehyde accounting for 3.0 wt. %, methyl glyoxylate which is a glyoxylate, accounting for 20.0 wt. %, and methyl glycolate which is a glycolate, accounting for 2.0 wt. %, were supplied as starting material (crude glyoxylate) to a low-boiling-point component distillation device, and light-boiling-point components including water were removed by coarse distillation in predetermined conditions. By doing so, a bottom product composed of 20.9 wt. % of methanol, 15.0 wt. % of water, 2.1 wt. % of formaldehyde, 56.1 wt. % of methyl glyoxylate, and 5.9 wt. % of methyl glycolate was obtained. Here, a mass balance of the glyoxylate in the whole system was 100 wt. %.

(2) Azeotropic Dehydration Process

Then, a predetermined quantity of n-propyl acetate as an azeotropic agent was added to the bottom product thus obtained through the above operation, and a mixture composed of 5.4 wt. % of methanol, 3.9 wt. % of water, 0.6 wt. % of formaldehyde, 14.5 wt. % of methyl glyoxylate, 1.5 wt. % of methyl glycolate, and 74.1 wt. % of n-propyl acetate was obtained.

Subsequently, the mixture was supplied to an azeotropic dehydration column 2 having 30 stages in a condensing section, 20 stages in a recovering section, and an inside diameter of 30 mm, at a rate of 0.45 kg/h, so that the mixture was subjected to azeotropic distillation (azeotropic dehydration). Here, a pressure inside the system was maintained at 300 mmHg, and temperatures at a material supply stage, a column bottom, and a column top were 80° C., 150° C., and 75° C., respectively.

As a result, a bottom product composed of 6.7 wt. % of methanol, 0.1 wt. % of water, 84.2 wt. % of methyl glyoxylate, 8.9 wt. % of methyl glycolate, and 0.1 wt. % of n-propyl acetate was obtained from the column bottom, while a distillate composed of 5.2 wt. % of methanol, 4.7 wt. % of water, 0.6 wt. % of formaldehyde, and 89.5 wt. % of n-propyl acetate was obtained from the column top. A mass balance of the methyl glyoxylate before and after the above operation was 100 wt. %.

(3) Fractionating Process

Subsequently, the bottom product obtained through the azeotropic dehydration process was supplied to a fractionating distillation column 3 having 50 stages in a condensing section, 20 stages in a recovering section and an inside diameter of 30 mm, at a rate of 0.45 kg/h, so that methyl glyoxylate was obtained by the fractionating. Here, a pressure inside the system and a reflux ratio were maintained at 600 mmHg and 10, respectively, while temperatures at a material supply stage, a column bottom, and a column top were 120° C., 155° C., and 110° C., respectively.

As a result, methyl glyoxylate with a purity of 99.4 percent was obtained from the column top, and in this fraction, 0.1 wt. % of methanol, 0.2 wt. % of water, and 0.3 wt. % of n-propyl acetate were contained as impurities. From the column bottom, a bottom product composed of 11.5 wt. % of methanol, 0.1 wt. % of water, 73.0 wt. % of methyl glyoxylate, and 15.4 wt. % of methyl glycolate was obtained. A mass balance of the methyl glyoxylate before and after the above fractionating operation was 100 wt. %.

[EXAMPLE 2]

(1) Coarse distillation Process

Light-boiling-point components including water were removed by the same operation as that in Example 1 except that a starting material (crude glyoxylate) composed of the following was used: 50.0 wt. % of methanol; 22.0 wt. % of water; 4.0 wt. % of formaldehyde; 18.0 wt. % of methyl glyoxylate; and 6.0 wt. % of methyl glycolate.

As a result, a bottom product composed of 19.7 wt. % of methanol, 14.2 wt. % of water, 1.9 wt. % of formaldehyde, 47.5 wt. % of methyl glyoxylate, and 16.7 wt. % of methyl glycolate was obtained. Here, a mass balance of the glyoxylate in the whole system was 100 wt. %.

(2) Azeotropic Dehydration Process

Then, a predetermined quantity of n-propyl acetate as an azeotropic agent was added to the bottom product thus obtained through the above operation, and a mixture composed of 2.5 wt. % of methanol, 1.8 wt. % of water, 0.2 wt. % of formaldehyde, 6.0 wt. % of methyl glyoxylate, 2.1 wt. % of methyl glycolate, and 87.4 wt. % of n-propyl acetate was obtained. The mixture was supplied to the same azeotropic dehydration column 2 as that in Example 1, at a rate of 0.45 kg/h, so that the mixture was subjected to azeotropic distillation. Here, a pressure inside the system was maintained at 300 mmHg, and temperatures at a material supply stage, a column bottom, and a column top were 72° C., 150° C., and 65° C., respectively.

As a result, a bottom product composed of 6.1 wt. % of methanol, 0.1 wt. % of water, 69.4 wt. % of methyl glyoxylate, and 24.4 wt. % of methyl glycolate was obtained from the column bottom, while a distillate composed of 2.1 wt. % of methanol, 1.9 wt. % of water, 0.3 wt. % of formaldehyde, and 95.7 wt. % of n-propyl acetate was obtained from the column top. A mass balance of the methyl glyoxylate before and after the above operation was 100 wt. %.

(3) Fractionating Process

Subsequently, the bottom product obtained through the azeotropic dehydration process was supplied to the same fractionating distillation column 3 as that in Example 1, at a rate of 0.45 kg/h, so that methyl glyoxylate was obtained by the fractionating. Here, a pressure inside the system and a reflux ratio were maintained at 600 mmHg and 10, respectively, while temperatures at a material supply stage, a column bottom, and a column top were 119° C., 155° C., and 110° C., respectively.

As a result, methyl glyoxylate with a purity of 99.8 percent was obtained from the column top, and in this fraction, 0.1 wt. % of methanol and 0.1 wt. % of water were contained as impurities. From the column bottom, a bottom product composed of 9.2 wt. % of methanol, 0.1 wt. % of water, 53.3 wt. % of methyl glyoxylate, and 37.4 wt. % of methyl glycolate was obtained. A mass balance of the methyl glyoxylate before and after the above fractionating operation was 100 wt. %.

[EXAMPLE 3]

(1) Azeotropic Dehydration Process

A predetermined quantity of isopropyl acetate as an azeotropic agent was added to a bottom product obtained through the same operation as that in the coarse distillation process of Example 1, which is composed of 20.9 wt. % of methanol, 15.0 wt. % of water, 2.1 wt. % of formaldehyde, 56.1 wt. % of methyl glyoxylate, and 5.9 wt. % of methyl glycolate. Then, a mixture composed of 4.5 wt. % of methanol, 3.3 wt. % of water, 0.5 wt. % of formaldehyde, 12.2 wt. % of methyl glyoxylate, 1.3 wt. % of methyl glycolate, and 78.2 wt. % of isopropyl acetate was obtained.

The mixture was supplied to the same azeotropic dehydration column 2 as that in Example 1, at a rate of 0.45 kg/h, so that the mixture was subjected to azeotropic distillation. Here, a pressure inside the system was maintained at 300 mmHg, and temperatures at a material supply stage, a column bottom, and a column top were 75° C., 145° C., and 69° C., respectively.

As a result, a bottom product composed of 6.3 wt. % of methanol, 0.1 wt. % of water, 84.7 wt. % of methyl glyoxylate, and 8.9 wt. % of methyl glycolate was obtained from the column bottom, while a distillate composed of 4.2 wt. % of methanol, 3.8 wt. % of water, 0.5 wt. % of formaldehyde, and 91.5 wt. % of isopropyl acetate was obtained from the column top. A mass balance of the methyl glyoxylate before and after the above operation was 100 wt. %.

(2) Fractionating Process

Subsequently, the bottom product obtained through the azeotropic dehydration process was supplied to the same fractionating distillation column 3 as that in Example 1, at a rate of 0.45 kg/h, so that methyl glyoxylate was obtained by the fractionating. Here, a pressure inside the system and a reflux ratio were maintained at 600 mmHg and 10, respectively, while temperatures at a material supply stage, a column bottom, and a column top were 120° C., 155° C., and 110° C., respectively. As a result, methyl glyoxylate with a purity of 99.8 percent was obtained from the column top, and in this fraction, 0.1 wt. % of methanol and 0.1 wt. % of water were contained as impurities. From the column bottom, a bottom product composed of 10.5 wt. % of methanol, 0.1 wt. % of water, 74.6 wt. % of methyl glyoxylate, and 14.8 wt. % of methyl glycolate was obtained. A mass balance of the methyl glyoxylate before and after the above fractionating operation was 100 wt. %.

[COMPARATIVE EXAMPLE 1]

(1) Azeotropic Dehydration Process

A predetermined quantity of dichloromethane as an azeotropic agent for comparison was added to a bottom product obtained through the same operation as that in the coarse distillation process of Example 1, which is composed of 20.9 wt. % of methanol, 15.0 wt. % of water, 2.1 wt. % of formaldehyde, 56.1 wt. % of methyl glyoxylate, and 5.9 wt. % of methyl glycolate. Then, a mixture composed of 1.3 wt. % of methanol, 0.9 wt. % of water, 0.1 wt. % of formaldehyde, 3.6 wt. % of methyl glyoxylate, 0.4 wt. % of methyl glycolate, and 93.7 wt. % of dichloromethane was obtained.

The mixture was supplied to the same azeotropic dehydration column 2 as that in Example 1, at a rate of 0.45 kg/h, so that the mixture was subjected to azeotropic distillation. Here, a pressure inside the system was maintained at 300 mmHg, and temperatures at a material supply stage, a column bottom, and a column top were 20° C., 150° C., and 17° C., respectively.

As a result, a bottom product composed of 8.6 wt. % of methanol, 1.7 wt. % of water, 81.2 wt. % of methyl glyoxylate, and 8.5 wt. % of methyl glycolate was obtained from the column bottom, while a distillate composed of 1.0 wt. % of methanol, 0.9 wt. % of water, 0.1 wt. % of formaldehyde, and 98.0 wt. % of dichloromethane was obtained from the column top. A mass balance of the methyl glyoxylate before and after the above operation was 100 wt. %.

(2) Fractionating Process

Subsequently, the bottom product obtained through the azeotropic dehydration process was subjected to fractionating in the same manner as that in Example 1 by the use of the same fractionating distillation column 3 as that in Example 1, so that methyl glyoxylate was obtained.

As a result, methyl glyoxylate with a purity of 97.7 percent was obtained from the column top, and in this fraction, 0.2 wt. % of methanol and 2.1 wt. % of water were contained as impurities. From the column bottom, a bottom product composed of 14.5 wt. % of methanol, 1.5 wt. % of water, 69.4 wt. % of methyl glyoxylate, and 14.6 wt. % of methyl glycolate was obtained. A mass balance of the methyl glyoxylate before and after the above fractionating operation was 100 wt. %.

[COMPARATIVE EXAMPLE 2]

(1) Azeotropic Dehydration Process

Cyclohexane as an azeotropic agent for comparison was added to a bottom product obtained through the same operation as that in the coarse distillation process of Example 1, which is composed of 20.9 wt. % of methanol, 15.0 wt. % of water, 2.1 wt. % of formaldehyde, 56.1 wt. % of methyl glyoxylate, and 5.9 wt. % of methyl glycolate. Then, a mixture composed of 2.5 wt. % of methanol, 1.8 wt. % of water, 0.2 wt. % of formaldehyde, 6.7 wt. % of methyl glyoxylate, 0.7 wt. % of methyl glycolate, and 88.1 wt. % of cyclohexane was obtained.

The mixture was supplied to the same azeotropic dehydration column 2 as that in Example 1, at a rate of 0.45 kg/h, so that the mixture was subjected to azeotropic distillation. Here, a pressure inside the system was maintained at 300 mmHg, and temperatures at a material supply stage, a column bottom, and a column top were 53° C., 150° C., and 45° C., respectively.

As a result, a bottom product composed of 7.7 wt. % of methanol, 2.0 wt. % of water, 81.7 wt. % of methyl glyoxylate, and 8.6 wt. % of methyl glycolate was obtained from the column bottom, while a distillate composed of 2.0 wt. % of methanol, 1.8 wt. % of water, 0.3 wt. % of formaldehyde, and 95.9 wt. % of cyclohexane was obtained from the column top. A mass balance of the methyl glyoxylate before and after the above operation was 100 wt. %.

(2) Fractionating Process

Subsequently, the bottom product obtained through the azeotropic dehydration process was subjected to fractionating in the same manner as that in Example 1 by the use of the same fractionating distillation column 3 as that in Example 1, so that methyl glyoxylate was obtained. As a result, methyl glyoxylate with a purity of 97.5 percent was obtained from the column top, and in this fraction, 0.2 wt. % of methanol and 2.3 wt. % of water were contained as impurities. From the column bottom, a bottom product composed of 13.2 wt. % of methanol, 1.7 wt. % of water, 70.3 wt. % of methyl glyoxylate, and 14.8 wt. % of methyl glycolate was obtained. A mass balance of the methyl glyoxylate before and after the above fractionating operation was 100 wt. %.

As clear from the results of the examples and the comparative examples, by the purifying method of the present invention, high-purity glyoxylates can be obtained from crude glyoxylates.

[EXAMPLE 4]

(1) Coarse distillation Process

Methanol accounting for 35.8 wt. %, water accounting for 24.7 wt. %, formaldehyde accounting for 6.4 wt. %, methyl glyoxylate which is a glyoxylate, accounting for 28.8 wt. %, and methyl glycolate which is a glycolate, accounting for 4.3 wt. %, were supplied as starting material (crude glyoxylate) at a rate of 0.2 kg/h to a thin film evaporator of the forced-agitation liquid-film type having a 450 $cm^2$ heating surface.

Here, a temperature of the heating surface was set to 90° C., and a pressure inside was maintained at 350 mmHg (47 kPa). As a result, a distillate composed of 54.7 wt. % of methanol, 36.7 wt. % of water, 6.4 wt. % of formaldehyde, and 2.2 wt. % of methyl glyoxylate was obtained from the column top, while a bottom product composed of 22.7 wt. % of methanol, 16.5 wt. % of water, 6.4 wt. % of formaldehyde, 47.2 wt. % of methyl glyoxylate, and 7.3 wt. % of methyl glycolate was obtained from the column bottom.

Here, no glyoxylic acid was produced due to hydrolyzation of methyl glyoxylate, and a mass balance of methyl glyoxylate through the coarse distillation process was 100 wt. %.

(2) Azeotropic Dehydration Process

Then, n-propyl acetate as an azeotropic agent was added to the bottom product thus obtained through the above operation, and a mixture composed of 10.3 wt. % of methanol, 7.4 wt. % of water, 2.9 wt. % of formaldehyde, 21.3 wt. % of methyl glyoxylate, 3.3 wt. % of methyl glycolate, and 54.8 wt. % of n-propyl acetate was obtained.

Subsequently, the mixture was supplied to an azeotropic dehydration column 2 having 30 stages in a condensing section, 20 stages in a recovering section, and an inside diameter of 30 mm, at a rate of 0.25 kg/h, so that the mixture was subjected to azeotropic dehydration. Here, a pressure inside the system and a reflux ratio were maintained at the atmospheric pressure and 0.2, respectively, while temperatures at a material supply stage, a column bottom, and a column top were 116° C., 157° C., and 85° C., respectively.

As a result, a bottom product composed of 4.0 wt. % of methanol, 0.1 wt. % of water, 83.0 wt. % of methyl glyoxylate, 12.9 wt. % of methyl glycolate, and 0.1 wt. % of n-propyl acetate was obtained from the column bottom, while a distillate composed of 12.4 wt. % of methanol, 10.0 wt. % of water, 3.9 wt. % of formaldehyde, and 73.7 wt. % of n-propyl acetate was obtained from the column top. A mass balance of the methyl glyoxylate before and after the above operation was 100 wt. %.

(3) Fractionating Process

Subsequently, the bottom product obtained through the above azeotropic dehydration process was supplied to a fractionating distillation column 3 having 50 stages in a condensing section (height of packing section of 1200 mmL), 20 stages (height of packing section of 300 mmL) in a recovering section, and an inside diameter of 24 mm, at a rate of 0.13 kg/h, so that methyl glyoxylate was obtained by the fractionating. Here, a pressure inside the system and a reflux ratio were maintained at 600 mmHg (80 kPa) and 3, respectively, while temperatures at a material supply stage, a column bottom, and a column top were 124° C., 165° C., and 113° C., respectively.

As a result, methyl glyoxylate with a purity of 99.7 percent was obtained from the column top, and in this fraction, 0.1 wt. % of methanol, 0.1 wt. % of water, and 0.1 wt. % of n-propyl acetate were contained as impurities. From the column bottom, a bottom product composed of 5.3 wt. % of methanol, 0.1 wt. % of water, 77.4 wt. % of methyl glyoxylate, and 17.0 wt. % of methyl glycolate was obtained. A mass balance of the methyl glyoxylate before and after the above fractionating operation was 100 wt. %.

[EXAMPLE 5]

(1) Coarse distillation Process

The same coarse distillation process as that in Example 4 was carried out except that a starting material composed of 35.4 wt. % of methanol, 25.4 wt. % of water, 3.4 wt. % of formaldehyde, 30.5 wt. % of methyl glyoxylate, and 5.3 wt. % of methyl glycolate was used, and that a temperature of the heating surface was set to 120° C. As a result, a distillate composed of 52.3 wt. % of methanol, 35.8 wt. % of water, 4.0 wt. % of formaldehyde, and 6.5 wt. % of methyl glyoxylate was obtained from the column top, while a bottom product composed of 15.7 wt. % of methanol, 12.9 wt. % of water, 2.7 wt. % of formaldehyde, 58.8 wt. % of methyl glyoxylate, and 9.9 wt. % of methyl glycolate was obtained from the column bottom.

Here, no glyoxylic acid was produced due to hydrolyzation of methyl glyoxylate, and a mass balance of methyl glyoxylate through the coarse distillation process was 100 wt. %.

(2) Azeotropic Dehydration Process n-propyl acetate as an azeotropic agent was added to the bottom product thus obtained through the above operation, and a mixture composed of 8.1 wt. % of methanol, 6.6 wt. % of water, 1.4 wt. % of formaldehyde, 30.1 wt. % of methyl glyoxylate, 5.1 wt. % of methyl glycolate, and 48.7 wt. % of n-propyl acetate was obtained. The azeotropic dehydration operation was carried out in the same manner as that in Example 4 except that this mixture was used.

As a result, a bottom product composed of 2.2 wt. % of methanol, 0.1 wt. % of water, 83.5 wt. % of methyl glyoxylate, 14.0 wt. % of methyl glycolate, and 0.1 wt. % of n-propyl acetate was obtained from the column bottom, while a distillate composed of 11.3 wt. % of methanol, 10.3 wt. % of water, 2.2 wt. % of formaldehyde, and 76.2 wt. % of n-propyl acetate was obtained from the column top. A mass balance of the methyl glyoxylate before and after the above operation was 100 wt. %.

(3) Fractionating Process

Subsequently, the bottom product obtained through the above azeotropic dehydration process was subjected to the same fractionating process as that in Example 1. As a result, methyl glyoxylate with a purity of 99.8 percent was obtained from the column top, and in this fraction, 0.1 wt. % of water and 0.1 wt. % of n-propyl acetate were contained as impurities. From the column bottom, a bottom product composed of 2.9 wt. % of methanol, 0.1 wt. % of water, 78.1 wt. % of methyl glyoxylate, and 18.8 wt. % of methyl glycolate was obtained. A mass balance of the methyl glyoxylate before and after the above fractionating operation was 100 wt. %.

[EXAMPLE 6]

(1) Coarse distillation Process

Methanol accounting for 37.0 wt. %, water accounting for 26.1 wt. %, formaldehyde accounting for 3.5 wt. %, methyl glyoxylate accounting for 28.4 wt. %, and methyl glycolate accounting for 5.0 wt. % were used as starting material (crude glyoxylate). The material was subjected to the same coarse distillation process as that in Example 5, except that a packed column for recovery of methyl glyoxylate, which has a height of packing section of 150 mm corresponding to 3 distillation stages, was connected with the thin film evaporator at a vapor outlet thereof, and that a reflux ratio was set to 0.2.

As a result, a distillate composed of 56.5 wt. % of methanol, 38.2 wt. % of water, and 5.3 wt. % of formaldehyde was obtained from the column top, while a bottom product composed of 12.2 wt. % of methanol, 10.7 wt. % of water, 1.2 wt. % of formaldehyde, 64.5 wt. % of methyl glyoxylate, and 11.4 wt. % of methyl glycolate was obtained from the column bottom.

Here, no glyoxylic acid was produced due to hydrolyzation of methyl glyoxylate, and a mass balance of methyl glyoxylate through the coarse distillation process was 100 wt. %.

(2) Azeotropic Dehydration Process n-propyl acetate as an azeotropic agent was added to the bottom product thus obtained through the above operation, and a mixture composed of 6.8 wt. % of methanol, 6.0 wt. % of water, 0.7 wt. % of formaldehyde, 36.1 wt. % of methyl glyoxylate, 6.4 wt. % of methyl glycolate, and 44.1 wt. % of n-propyl acetate was obtained. The azeotropic dehydration operation was carried out in the same manner as that in Example 4 except that this mixture was used.

As a result, a bottom product composed of 1.6 wt. % of methanol, 0.1 wt. % of water, 83.5 wt. % of methyl glyoxylate, 14.8 wt. % of methyl glycolate, and 0.1 wt. % of n-propyl acetate was obtained from the column bottom, while a distillate composed of 10.8 wt. % of methanol, 10.5 wt. % of water, 1.2 wt. % of formaldehyde, and 77.6 wt. % of n-propyl acetate was obtained from the column top. A mass balance of the methyl glyoxylate before and after the above operation was 100 wt. %.

(3) Fractionating Process

Subsequently, the bottom product obtained through the above azeotropic dehydration process was subjected to the fractionating process in the same manner as that in Example 4. As a result, methyl glyoxylate with a purity of 99.8 percent was obtained from the column top, and in this fraction, 0.1 wt. % of water and 0.1 wt. % of n-propyl acetate were contained as impurities. From the column bottom, a bottom product composed of 2.1 wt. % of methanol, 0.1 wt. % of water, 78.1 wt. % of methyl glyoxylate, and 19.7 wt. % of methyl glycolate was obtained. A mass balance of the methyl glyoxylate before and after the above fractionating operation was 100 wt. %.

[EXAMPLE 7]

(1) Coarse distillation Process

The same coarse distillation operation was carried out except that methanol accounting for 35.8 wt. %, water accounting for 24.7 wt. %, formaldehyde accounting for 6.4 wt. %, methyl glyoxylate accounting for 28.8 wt. %, and methyl glycolate accounting for 4.3 wt. % were used as starting material (crude glyoxylates).

As a result, a distillate composed of 54.7 wt. % of methanol, 36.7 wt. % of water, 6.4 wt. % of formaldehyde, and 2.2 wt. % of methyl glyoxylate was obtained from the column top, while a bottom product composed of 22.7 wt. % of methanol, 16.5 wt. % of water, 6.4 wt. % of formaldehyde, 47.2 wt. % of methyl glyoxylate, and 7.3 wt. % of methyl glycolate was obtained from the column bottom.

Here, no glyoxylic acid was produced due to hydrolyzation of methyl glyoxylate, and a mass balance of methyl glyoxylate through the coarse distillation process was 100 wt. %.

(2) Azeotropic Dehydration Process

Cyclohexane as an azeotropic agent was added to the bottom product thus obtained through the above operation, and a mixture composed of 7.2 wt. % of methanol, 5.2 wt. % of water, 2.0 wt. % of formaldehyde, 15.0 wt. % of methyl glyoxylate, 2.3 wt. % of methyl glycolate, and 68.3 wt. % of cyclohexane was obtained. The azeotropic dehydration operation was carried out in the same manner as that in Example 4 except that this mixture was used.

As a result, a bottom product composed of 4.0 wt. % of methanol, 1.3 wt. % of water, 82.1 wt. % of methyl glyoxylate, 12.6 wt. % of methyl glycolate, and a trace of cyclohexane was obtained from the column bottom, while a distillate composed of 7.9 wt. % of methanol, 6.1 wt. % of water, 2.5 wt. % of formaldehyde, and 83.5 wt. % of cyclohexane was obtained from the column top. A mass balance of the methyl glyoxylate before and after the above operation was 100 wt. %.

(3) Fractionating Process

Subsequently, the bottom product obtained through the above azeotropic dehydration process was subjected to the fractionating process in the same manner as that in Example 4. As a result, methyl glyoxylate with a purity of 98.9 percent was obtained from the column top, and in this fraction, 0.1 wt. % of water, 1.1 wt. % of methanol, and a trace of cyclohexane were contained as impurities. From the column bottom, a bottom product composed of 5.2 wt. % of methanol, 1.4 wt. % of water, 76.2 wt. % of methyl glyoxylate, and 16.8 wt. % of methyl glycolate was obtained. A mass balance of the methyl glyoxylate before and after the above fractionating operation was 100 wt. %.

[CONVENTIONAL EXAMPLE 1]

(1) Coarse distillation Process

The same crude glyoxylate as that in Example 1 was supplied to a tray-type distillation column having 10 stages, at a rate of 0.2 kg/h. Here, a pressure inside the system was maintained at 350 mmHg, while temperatures at a material supply stage, a column bottom, and a column top were 70° C., 75° C., and 62° C. As a result, a distillate composed of 61.8 wt. % of methanol, 31.7 wt. % of water, and 6.5 wt. % of formaldehyde was obtained from the column top, while a bottom product composed of 9.7 wt. % of methanol, 14.5 wt. % of water, 6.4 wt. % of formaldehyde, 52.3 wt. % of methyl glyoxylate, 9.2 wt. % of methyl glycolate, and 7.9 wt. % of glyoxylic acids was obtained from the column bottom.

Here, a mass balance of methyl glyoxylate through the distillation operation as the coarse distillation process was 85 wt. %, and the rest 15 wt. % was lost through the production of glyoxylic acids due to hydrolyzation of methyl glyoxylate.

(2) Azeotropic Dehydration Process

Then, cyclohexane as an azeotropic agent was added to the bottom product thus obtained through the above operation, and a mixture composed of 3.4 wt. % of methanol, 5.0 wt. % of water, 2.2 wt. % of formaldehyde, 18.1 wt. % of methyl glyoxylate, 3.2 wt. % of methyl glycolate, 2.7 wt. % of glyoxylic acids, and 65.5 wt. % of cyclohexane was obtained. The azeotropic dehydration operation was carried out in the same manner as that in Example 1, except that this mixture was used.

As a result, a bottom product composed of 1.4 wt. % of methanol, 1.1 wt. % of water, 73. 5 wt. % of methyl glyoxylate, 13.0 wt. % of methyl glycolate, 11.2 wt. % of unknown components, and a trace of cyclohexane was obtained from the column bottom, while a distillate composed of 4.0 wt. % of methanol, 6.3 wt. % of water, 2.9 wt. % of formaldehyde, and 86.8 wt. % of cyclohexane was obtained from the column top.

(3) Fractionating Process

Subsequently, the bottom product obtained through the above azeotropic dehydration process was subjected to the same fractionating operation as that in Example 1. As a result, methyl glyoxylate with a purity of 98.8 percent was obtained from the column top, and in this fraction, 0.1 wt. % of methanol, 1.1 wt. % of water, and a trace of cyclohexane were contained as impurities. From the column bottom, a bottom product composed of 1.8 wt. % of methanol, 1.1 wt. % of water, 65.0 wt. % of methyl glyoxylate, 17.2 wt. % of methyl glycolate, and 14.8 wt. % of unknown components was obtained.

[EXAMPLE 8]

(1) Coarse distillation Process

Methanol accounting for 35.8 wt. %, water accounting for 24.7 wt. %, formaldehyde accounting for 6.4 wt. %, methyl glyoxylate accounting for 28.8 wt. %, and methyl glycolate accounting for 4.3 wt. % were, as starting material (crude glyoxylate), supplied to the same forced-agitation thin-film type evaporator (low-boiling-point component distillation device) as that in Example 4, where low-boiling-point components including water were removed. By doing so, a bottom product composed of 22.7 wt. % of methanol, 16.5 wt. % of water, 6.4 wt. % of formaldehyde, 47.2 wt. % of methyl glyoxylate, and 7.2 wt. % of methyl glycolate was obtained.

Here, no glyoxylic acid was produced due to hydrolyzation of methyl glyoxylate, and a mass balance of methyl glyoxylate through the coarse distillation process was 100 wt. %.

(2) Azeotropic Dehydration Process n-propyl acetate as an azeotropic agent was added to the bottom product thus obtained through the above operation, and a mixture composed of 10.3 wt. % of methanol, 7.4 wt. % of water, 2.9 wt. % of formaldehyde, 21.3 wt. % of methyl glyoxylate, 3.3 wt. % of methyl glycolate, and 54.8 wt. % of n-propyl acetate was obtained.

Subsequently, the mixture was supplied to a tray column (azeotropic dehydration column) having 30 stages in a condensing section, 20 stages in a recovering section, and an inside diameter of 30 mm, at a rate of 0.25 kg/h, so that the mixture was subjected to azeotropic dehydration. Here, a pressure inside the system and a reflux ratio were set to atmospheric pressure and 0.3, respectively, while temperatures at a material supply stage, a column bottom, and a column top were 116° C., 157° C., and 85° C., respectively.

As a result, a bottom product composed of 4.0 wt. % of methanol, 0.1 wt. % of water, 83.0 wt. % of methyl glyoxylate, 12.8 wt. % of methyl glycolate, and 0.1 wt. % of n-propyl acetate was obtained from the column bottom, while a distillate composed of 12.4 wt. % of methanol, 10.0 wt. % of water, 3.9 wt. % of formaldehyde, and 73.7 wt. % of n-propyl acetate was obtained from the column top. A mass balance of the methyl glyoxylate before and after the above operation was 100 wt. %.

(3) Fractionating Process

Subsequently, the bottom product obtained through the above azeotropic dehydration process was supplied to a fractionating distillation-use packed column having 50 stages in a condensing section, 20 stages in a recovery section, and an inside diameter of 30 mm, at a rate of 0.2 kg/h. Herein, a pressure inside the system and a reflux ratio were set to 600 mmHg (80 kPa) and 3, respectively, while temperatures at a material supply stage, a column bottom, and a column top were 124° C., 165° C., and 113° C., respectively.

As a result, methyl glyoxylate with a purity of 99.7 percent was obtained from the column top, and in this fraction, 0.1 wt. % of methanol, 0.1 wt. % of water, and 0.1 of n-propyl acetate were contained as impurities. From the column bottom, a bottom product composed of 5.3 wt. % of methanol, 0.1 wt. % of water, 77.4 wt. % of methyl glyoxylate, and 17.0 wt. % of methyl glycolate was obtained. A mass balance of the methyl glyoxylate before and after the above fractionating operation was 100 wt. %.

[EXAMPLE 9]

(1) Coarse distillation Process

By carrying out the coarse distillation process in the same manner as that in Example 8, a bottom product composed of 22.7 wt. % of methanol, 16.5 wt. % of water, 6.4 wt. % of formaldehyde, 47.2 wt. % of methyl glyoxylate, and 7.2 wt. % of methyl glycolate was obtained.

Here, no glyoxylic acid was produced due to hydrolyzation of methyl glyoxylate, and a mass balance of methyl glyoxylate through the coarse distillation process was 100 wt. %.

(2) Azeotropic Dehydration Process

The bottom product obtained through the fractionating operation in Example 8 was added to the bottom product obtained through the above coarse distillation operation, and n-propyl acetate as an azeotropic agent was also added thereto. As a result, a mixture composed of 7.6 wt. % of methanol, 3.6 wt. % of water, 1.4 wt. % of formaldehyde, 50.2 wt. % of methyl glyoxylate, 10.4 wt. % of methyl glycolate, and 26.2 wt. % of n-propyl acetate was obtained.

Subsequently, the mixture was subjected to the same azeotropic dehydration operation as that in Example 8. As a result, a bottom product composed of 5.5 wt. % of methanol, 0.1 wt. % of water, 81.3 wt. % of methyl glyoxylate, 16.8 wt. % of methyl glycolate, and 0.1 wt. % of n-propyl acetate was obtained from the column bottom, while a distillate composed of 10.9 wt. % of methanol, 9.1 wt. % of water, 3.6 wt. % of formaldehyde, and 68.4 wt. % of n-propyl acetate was obtained from the column top. A mass balance of the methyl glyoxylate before and after the above operation was 100 wt. %.

(3) Fractionating Process

Subsequently, the bottom product obtained through the above azeotropic dehydration process was subjected to the same fractionating operation as that in Example 8. As a result, methyl glyoxylate with a purity of 99.5 percent was obtained from the column top, and in this fraction, 0.1 wt. % of water, and 0.4 of n-propyl acetate were contained as impurities. From the column bottom, a bottom product composed of 6.9 wt. % of methanol, 0.1 wt. % of water, 73.8 wt. % of methyl glyoxylate, and 21.0 wt. % of methyl glycolate was obtained. A mass balance of the methyl glyoxylate before and after the above fractionating operation was 100 wt. %.

[EXAMPLE 10]

(1) Coarse distillation Process

By carrying out the coarse distillation process in the same manner as that in Example 8, a bottom product composed of 22.7 wt. % of methanol, 16.5 wt. % of water, 6.4 wt. % of formaldehyde, 47.2 wt. % of methyl glyoxylate, and 7.2 wt. % of methyl glycolate was obtained.

Here, no glyoxylic acid was produced due to hydrolyzation of methyl glyoxylate, and a mass balance of methyl glyoxylate through the coarse distillation process was 100 wt. %.

(2) Azeotropic Dehydration Process

By adding isopropyl acetate to the bottom product obtained through the above coarse distillation operation, a mixture composed of 6.5 wt. % of methanol, 4.7 wt. % of water, 1.8 wt. % of formaldehyde, 13.6 wt. % of methyl glyoxylate, 2.1 wt. % of methyl glycolate, and 71.2 wt. % of isopropyl acetate was obtained.

Subsequently, the mixture was supplied to the same azeotropic dehydration column as that in Example 8, at a rate of 0.3 kg/h. As a result, a bottom product composed of 1.9 wt. % of methanol, 0.2 wt. % of water, 64.4 wt. % of methyl glyoxylate, 9.9 wt. % of methyl glycolate, and 23.6 wt. % of isopropyl acetate was obtained from the column bottom, while a distillate composed of 7.8 wt. % of methanol, 6.0 wt. % of water, 2.3 wt. % of formaldehyde, and 83.9 wt. % of isopropyl acetate was obtained from the column top.

Subsequently, the bottom product obtained was again supplied to the same azeotropic dehydration column, at a rate of 0.2 kg/h. As a result, a bottom product composed of 1.6 wt. % of methanol, 0.1 wt. % of water, 85.2 wt. % of methyl glyoxylate, 13.1 wt. % of methyl glycolate, and a trace of isopropyl acetate was obtained from the column bottom, while a distillate composed of 2.8 wt. % of methanol, 0.4 wt. % of water, and 96.8 wt. % of isopropyl acetate was obtained from the column top. A mass balance of the methyl glyoxylate before and after the above operation was 100 wt. %.

(3) Fractionating Process

Subsequently, the bottom product obtained through the last azeotropic dehydration process was subjected to the same fractionating operation as that in Example 8. As a result, methyl glyoxylate with a purity of 99.5 percent was obtained from the column top, and in this fraction, 0.1 wt. % of water, and 0.1 wt. % of isopropyl acetate were contained as impurities. From the column bottom, a bottom product composed of 2.0 wt. % of methanol, 0.1 wt. % of water, 80.9 wt. % of methyl glyoxylate, and 17.0 wt. % of methyl glycolate was obtained. A mass balance of the methyl glyoxylate before and after the above fractionating operation was 100 wt. %.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

Industrial Applicability

The glyoxylate purifying method and the distillation device for purification of glyoxylates enable easy and efficient purification of high-purity glyoxylates that are suitably used as materials for synthesizing sodium polyglyoxylate which is an effective builder component for, for example, a surface active agent.

We claim:

1. A method for purifying a glyoxylate, comprising:

an azeotropic dehydration step of conducting azeotropic dehydration with respect to a crude glyoxylate in which water coexists, in the presence of an aliphatic ester as an azeotropic agent.

2. The method as set forth in claim 1, wherein said the aliphatic ester is a compound expressed as:

$$R_1COOR_2 \quad (2)$$

where $R_1$ represents a hydrogen, a methyl group, or an ethyl group, while $R_2$ represents an alkyl group with 1 to 4 carbons.

3. The method as set forth in claim 1, wherein the aliphatic ester is at least either n-propyl acetate or isopropyl acetate.

4. The method as set forth in claim 1, wherein:
a distillation column for azeotropic dehydration is used for said azeotropic dehydration step; and
said azeotropic dehydration step includes a sub-step of continuously supplying the crude glyoxylate to which the aliphatic ester has been added, to a middle stage of the distillation column.

5. The method as set forth in claim 1, wherein in said azeotropic dehydration step, the azeotropic dehydration operation is conducted a plurality of times.

6. A method for purifying a glyoxylate, comprising:
a coarse distillation step of continuously conducting coarse distillation with respect to a crude glyoxylate in a film form in which at least water coexists; and
a main distillation step of further distilling by azeotropic dehydratoin a glyoxylate-containing liquid obtained through the coarse purification by said coarse distillation step.

7. The method as set forth in claim 6, wherein a thin film evaporator is used for said coarse distillation step.

8. The method as set forth in claim 6, wherein said main distillation step includes:
an azeotropic dehydration sub-step for distillation in the presence of an azeotropic agent; and
a fractionating sub-step of further distilling a glyoxylate-containing liquid obtained through coarse purification by said azeotropic dehydration sub-step.

9. The method as set forth in claim 8, wherein the azeotropic agent is an aliphatic ester.

10. The method as set forth in claim 8, wherein in said azeotropic dehydration sub-step, the azeotropic dehydration operation is conducted a plurality of times.

11. The method as set forth in claim 6, wherein a pressure in said coarse distillation step is in a range of 4 kPa to 101 kPa.

* * * * *

UNITED STATES PATENT AND TRADEMARK OFFICE

CERTIFICATE OF CORRECTION

PATENT NO.   : 6,037,489
DATED        : March 14, 2000
INVENTOR(S)  : BABA et al It is certified that error appears in the above-identified patent and that said letters patent is hereby corrected as shown below:

Title Page Item [22] should read --[22] PCT filed: Aug. 29, 1997--

Signed and Sealed this

Twenty-fourth Day of April, 2001

Attest:

NICHOLAS P. GODICI

Attesting Officer

Acting Director of the United States Patent and Trademark Office